United States Patent [19]

Curry

[11] Patent Number: 5,059,288
[45] Date of Patent: Oct. 22, 1991

[54] RECOVERY OF ISOPROPYL ACETATE AND ETHANOL FROM AN ISOPROPYL ACETATE, ETHANOL AND WATER-CONTAINING STREAM

[75] Inventor: William J. Curry, Thornton, Pa.
[73] Assignee: Harborchem, Cranford, N.J.
[21] Appl. No.: 439,830
[22] Filed: Nov. 21, 1989
[51] Int. Cl.$^5$ .................. B01D 3/16; C07C 29/86; C07C 67/58
[52] U.S. Cl. .................. 203/43; 203/73; 203/98; 203/DIG. 11; 560/248; 568/918
[58] Field of Search .................. 203/43-46, 203/DIG. 11, 71, 73, 83, 14, 19, 98, 94; 560/248; 568/913, 918, 916

[56] References Cited

U.S. PATENT DOCUMENTS

| 1,536,545 | 5/1925 | Willkie | 560/248 |
| 1,898,737 | 2/1933 | Merley | 560/248 |
| 3,578,689 | 5/1971 | Martin et al. | 560/248 |
| 4,379,028 | 4/1983 | Berg et al. | 203/51 |
| 4,501,645 | 2/1985 | Berg et al. | 203/51 |
| 4,525,245 | 6/2585 | Berg et al. | 203/51 |
| 4,693,789 | 9/1987 | Berg et al. | 203/51 |
| 4,698,137 | 10/1987 | Berg | 203/51 |
| 4,715,932 | 12/1987 | Misselhorn et al. | 203/19 |

FOREIGN PATENT DOCUMENTS 125575 11/1984 European Pat. Off. ........... 560/248
54-119411 9/1979 Japan .

OTHER PUBLICATIONS 79.09.17, J54119411, JP 54-119411.

Primary Examiner—Wilbur Bascomb, Jr.
Attorney, Agent, or Firm—Coleman R. Reap

[57] ABSTRACT

High purity isopropyl acetate and ethanol are recovered from a process stream containing isopropyl acetate, ethanol and water by a multiple step process including extracting substantially all of the ethanol from the stream using water as a solvent, stripping the extract stream to remove substantially all of the remaining isopropyl acetate as an overhead recycle stream, which is combined with the fresh feed stream prior to the extraction step, fractionating the ethanol-rich stripping column bottoms stream to produce a ethanol-water azeotropic overhead stream and using a portion of the fractionating column bottoms stream as the solvent for the extraction step.

14 Claims, 3 Drawing Sheets 5,059,288

RECOVERY OF ISOPROPYL ACETATE AND ETHANOL FROM AN ISOPROPYL ACETATE, ETHANOL AND WATER-CONTAINING STREAM

FIELD OF THE INVENTION

This invention relates to the recovery of isopropyl acetate and more particularly to the recovery of isopropyl acetate and ethanol from an aqueous stream containing isopropyl acetate, ethanol and water.

BACKGROUND OF THE INVENTION

One of the most commonly employed methods for separating the components of organic liquid mixtures is distillation. However, distillation cannot be conveniently employed when the components which it is desired to separate have boiling points that are close together. For example, when the boiling points of the components of a liquid mixture are very close together, e.g. only a few degrees centigrade apart, it requires a distillation column having an inordinately high number of trays to effect good separation of the components. Separation of the components of a liquid mixture by distillation is impossible when the components form an azeotrope, i.e., a constant boiling mixture, because the distillate will always contain the components in the same ratio as the boiling mixture. When it is desired to separate two or more components of a liquid mixture which forms an azeotropic combination, means other than simple distillation must be resorted to. One alternate technique for the separation of the components of azeotropic liquid mixtures is solvent extraction. This method can often be used when one of the components is soluble in a third liquid and the other is not. It is often difficult, though, to find a liquid which is a good solvent for one liquid but a poor solvent for the other liquid of a two liquid mixture.

The separation of isopropyl acetate and ethanol from an isopropyl acetate-ethanol-water mixture, which is difficult because this system forms a ternary azeotropic mixture, is further complicated by the fact that isopropyl acetate and water, isopropyl acetate and ethanol and ethanol and water each form binary azeotropic mixtures. Furthermore, these azeotropes have boiling points that are only a few degrees apart. Specifically, the boiling point of the ternary azeotropic mixture is 74.8 degrees C., that of an isopropyl acetate-water azeotropic mixture is 76.6 degrees C., that of an isopropyl acetate-ethanol azeotropic mixture is 76.8 degrees C., and that of an ethanol-water azeotropic mixture is 78.2 degrees C. Thus it is clear that methods other than straight distillation must be used to recover isopropyl acetate and ethanol from this ternary system.

Isopropyl acetate is only slightly soluble in water, thus presenting the possibility of separating the above ternary system by means of extraction. However extraction alone does not generally provide a clean enough separation of the isopropyl acetate and ethanol. The present invention provides a process which permits the recovery of an isopropyl acetate stream which is substantially free of ethanol and an ethanol stream which is substantially free of isopropyl acetate.

PRIOR ART

U.S. Pat. Nos. 4,693,789 and 4,698,137, issued to Berg, disclose the separation of isopropyl acetate from isopropanol by extractive distillation using an organic nitrogeneous compound as the extraction agent. U.S. Pat. No. 4,501,645, also issued to Berg, discloses the separation of methanol from acetone by extractive distillation using one of several ketonic compounds as the extraction agent. U.S. Pat. No. 4,525,245, also issued to Berg, discloses the separation of butyl acetate from butanol by extractive distillation using certain oxygenated, nitrogenous and/or sulfur containing organic compounds as the extraction agent. Japanese patent J54119411A and J81038133B disclose the separation of methyl acetate from methanol by distillation in the presence of a diol having 2–5 carbon atoms.

OBJECTS OF THE INVENTION

It is an object of the invention to present an improved method of recovering high purity isopropyl acetate from a stream containing isopropyl acetate, ethanol and water.

It is another object of the invention to present an improved method of recovering high purity isopropyl acetate and ethanol from an azeotropic mixture containing isopropyl acetate, ethanol and water.

It is another object of the invention to present a method of rendering an aqueous process stream containing isopropyl acetate and ethanol more suitable for biological waste treatment processes.

These and other objects of the invention will become more apparent from the following description.

SUMMARY OF THE INVENTION

According to a preferred embodiment of the invention, the objects are achieved by the process of the invention which includes the steps of extracting ethanol from a feed stream comprising isopropyl acetate, ethanol and water using water as a solvent; stripping the extract stream to recover an overhead stream comprising isopropyl acetate, ethanol and water substantially at the ternary azeotropic concentration and a bottoms stream which is substantially free of isopropyl acetate; and fractionating the bottoms stream to recover a substantially isopropyl acetate-free overhead ethanol product and a high purity water bottoms stream. The overhead stream from the stripping unit is recycled to the extraction unit and the fractionating column bottoms stream is used as the solvent for the extraction step.

According to an alternate embodiment of the invention a feed mixture is extracted and the extract stripped as described above but fresh water is used as the extraction solvent and the stripper bottoms fractionation step is eliminated.

DETAILED DESCRIPTION OF THE INVENTION

Figure 1:
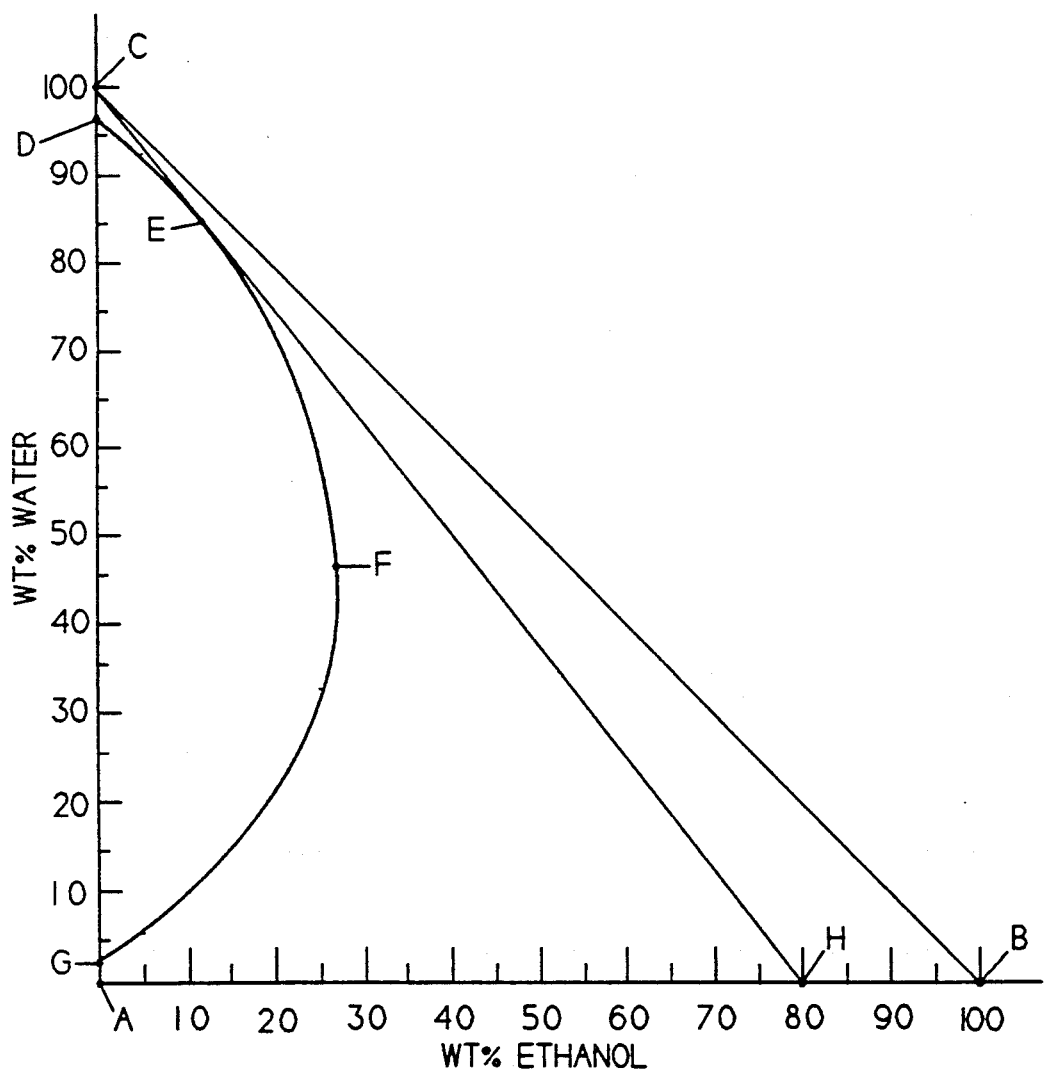
FIG. 1 is a phase diagram for the ternary system comprised of isopropyl acetate, ethanol and water.

The ternary system resolved by the process of this invention is shown in the phase diagram, FIG. 1, which was developed at 71° C. Points A, B, and C in FIG. 1 represent, respectively, the points at which the concentrations of isopropyl acetate, ethanol and water are 100%. Curved line DEFG represents the limit of mutual solubility of the three components. Mixtures having compositions falling outside of the envelope formed by curved line DEFG exist as a single phase. Mixtures having compositions theoretically falling within the envelope form two ternary phases whose compositions lie on curve DEFG. Line CH is tangent to curved line DEFG at point E. The ternary mixtures resolved by the extraction step of the process of the invention are those having a composition falling within the somewhat triangular zone bounded by straight lines AH and EH and curved line segment EFG. Such mixtures can be resolved by contacting the mixtures with water in sufficient quantity to bring the concentration of components within the envelope encompassed by curve DEFG. The location of points D and G and curve DEFG will, of course, vary with varying temperatures.

The process of the invention is particularly suitable for resolving aqueous feed mixtures comprising about 15 to about 90 weight percent isopropyl acetate and about 10 to about 70 weight percent ethanol.

The process of the invention can be carried out in an equipment train comprising, in the preferred embodiment, a solvent extractor, a stripping column and a fractionating column. A typical equipment train for practicing the process of the invention is illustrated schematically in FIG. 2.

Figure 2:
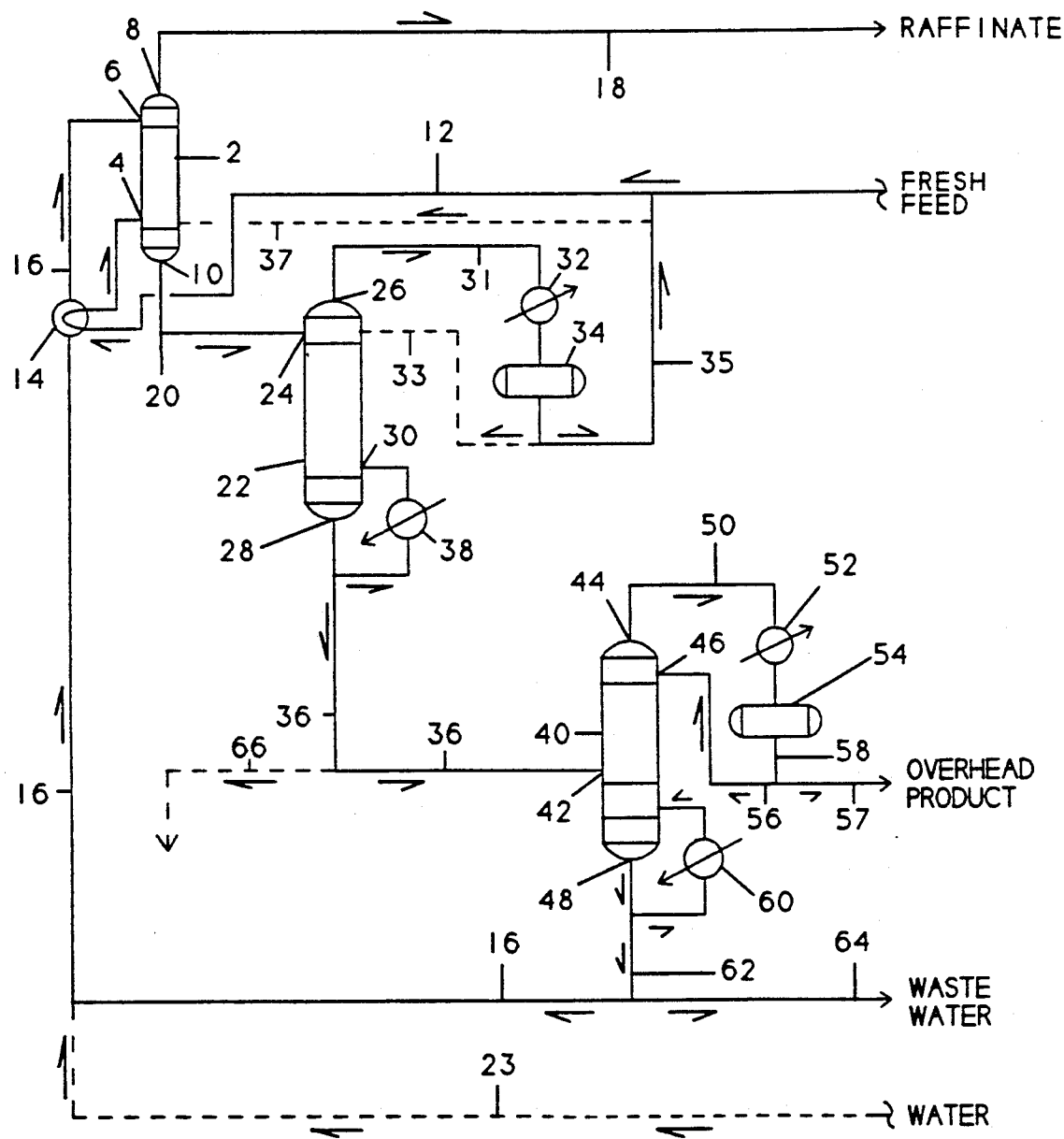
FIG. 2 is a schematic drawing of an extraction and distillation train for the separation of isopropyl acetate and ethanol by the preferred process of the invention.

Referring to FIG. 2, the first piece of equipment in the train is a solvent extractor 2, which is fitted with a feed inlet 4, a solvent inlet 6, a raffinate outlet 8, and an extract outlet 10. Extractor 2 is also equipped with a heat exchanger 14 for heating or cooling the extractor feed and solvent stream going to the extractor.

Extractor 2 can be any type of extractor equipment generally available for commercial operations. Typical extractors useful in the process of the invention include mixer-settlers; spray and packed columns; tray, baffle and agitated tower extractors; and pulse columns.

The second piece of equipment in the train is stripper 22, which is fitted with a feed inlet 24, an overhead outlet 26, a bottoms outlet 28 and a reboiler inlet 30. In the embodiment illustrated in FIG. 2, feed inlet 24 is located near the top of the stripper column. Stripper 22 receives, as a feed stream, the extract product from extractor 2 through line 20. Stripper 22 is also provided with an overhead condenser 32 and an accumulator 34, which respectively condense and collect the stripper overhead product stream exiting stripper 22 through line 31; and heat exchanger or reboiler 38, which heats a portion of the stripper bottoms stream and returns it to the bottom of the stripper 22 through inlet 30.

The third piece of equipment in the train illustrated in FIG. 2 is fractionator 40. This unit is employed when it is desired to recover an ethanol enriched stream. Fractionator 40, which can be a conventional fractionator having rectification and stripping sections, receives as its feed the bottoms product from stripper 22. Fractionator 40 is fitted with a feed inlet 42, an overhead outlet 44, a reflux inlet 46, and a bottoms outlet 48. Fractionator 40 is provided with a condenser 52 and a condensate accumulator 54. The outlet line 58 from accumulator 54 is connected both to reflux inlet 46 and the overhead product line. Fractionator 40 is equipped with a bottoms heat exchanger or reboiler 60 which returns heated bottoms product to fractionator 40. Bottoms product line 62, is joined to extractor solvent feed line 16 and waste water purge line 64.

In practicing the process of the invention, a feed mixture is fed into the system through extractor feed line 12. Minor amounts of other organic compounds, such as other esters, aldehydes, ketones and alcohols, may be present in the feed mixture, provided that they do not interfere with the operation of the process of the invention. The feed mixture passes through heat exchanger 14 wherein its temperature is adjusted to a value in the desired range. The temperature at which the extraction step is carried out is not critical, however it is generally preferred to operate the extractor at a temperature in the range of about 5 to 70 degrees C. Heat Exchanger 14 also serves to adjust the water solvent temperature.

The raffinate from the extractor leaves the extractor through outlet 8 and goes to product tankage through line 18. This stream is high purity isopropyl acetate and generally contains about 2 weight percent water and less than 1 weight percent ethanol. This is approximately the amount of water which is soluble in pure isopropyl acetate at the extractor operating temperature.

The extractor extract stream, which contains substantially all of the ethanol plus some isopropyl acetate, next enters a fractionator, which, as shown in FIG. 2, may be a stripping column. The purpose of the stripper 22 is to remove substantially all of the isopropyl acetate from the extract stream. The stripper feed can be introduced at the temperature at which it exits the extractor or, if desired, it can be heated. The overhead stream from the stripper column comprises substantially all of the remaining isopropyl acetate, plus ethanol and water, substantially at the ternary azeotropic concentration. The overhead stream is condensed in condenser 32 and collected in accumulator 34, from which it is recycled to the extractor through line 35 with fresh feed in line 12. Alternatively, the overhead stream can be separately recycled to the extractor through optional line 37, shown in dotted form. However, as explained below, the stripper overhead stream can be separately extracted in a batch type operation. If desired, a portion of the stream leaving accumulator 34 may be refluxed to the top of stripper 22 via optional line 33, also shown in dotted form. The bottoms product, which exits stripper 22 through bottoms outlet 28, contains substantially all of the ethanol present in the fresh feed stream and is substantially free of isopropyl acetate. A portion of the stripper bottoms product is recycled to the bottom of stripper 22 through reboiler 38 and, in the embodiment illustrated in FIG. 2, the balance is sent to fractionator 40 through fractionator feed line 36.

Feed enters fractionator 40 through fractionator feed inlet 42, which is generally located in the lower part of the fractionator. The function of fractionator 40 is to recover the ethanol in the stripper bottoms stream. Distillate leaves fractionator 40 via distillate line 50. The distillate passes through condenser 52 and into overhead accumulator 54. Condensate leaving accumulator 54 is split into a reflux stream, which is returned to the top of fractionator 40 through line 56 and reflux inlet 46, and an overhead product stream through line 57. The overhead product stream contains substantially all of the ethanol entering fractionator 40 and water, the water being present in an amount at or in excess of the azeotropic balance for this mixture at the existing conditions. The fractionator bottoms leaves fractionator 40 via line 62 through bottoms outlet 48. A portion of the bottoms stream is recycled to the bottom of fractionator 40 through reboiler 60. In the embodiment illustrated in FIG. 2 the remainder is split into an extractor solvent stream and a bottoms product waste water stream. The extractor solvent stream is returned to extractor 2 via line 16. The bottoms product waste water stream, which may contain a very small amount of ethanol, can be sent to treatment via line 64 to remove the ethanol, and isopropyl acetate, if any is present, and then disposed of.

In some cases it may be desirable to recover only a high purity isopropyl acetate stream. This can be accomplished by the process of the invention by eliminating the ethanol-water fractionation step carried out in fractionator 40. According to this embodiment, the bottoms stream from stripper 22 is disposed of through line 66, shown in dotted form or otherwise treated in any desired manner and water provided from a different source through optional line 23, shown in dotted form is used as the solvent in the extraction step.

The key to the success of the process of the invention is the surprisingly clean separation that is obtained in the fractionation of the extract stream leaving extractor 2. Since the ternary azeotropic mixture of this system has a boiling point about 2 degrees C. lower than the boiling point of the isopropyl acetate-ethanol binary azeotrope and about 3½ degrees C. lower than the boiling point of the ethanol-water binary azeotrope, it would be expected that a rectifying tower having about 125 theoretical stages and operating at a 14 to 1 reflux ratio would be required for the separation, and that even then an equal molar mixture of the ternary azeotrope and one or more of the binary azeotropes would be obtained. However, it has been found that a substantially clean separation of the ternary azeotrope from the other azeotropes is obtained by the process of the invention with as few as eleven theoretical stages and a reflux ratio of as low as 3 to 1. Furthermore, because of the ease of separation, any of the more simple fractionators, including batch-type stills, can be used in place of stripper 22.

Figure 3:
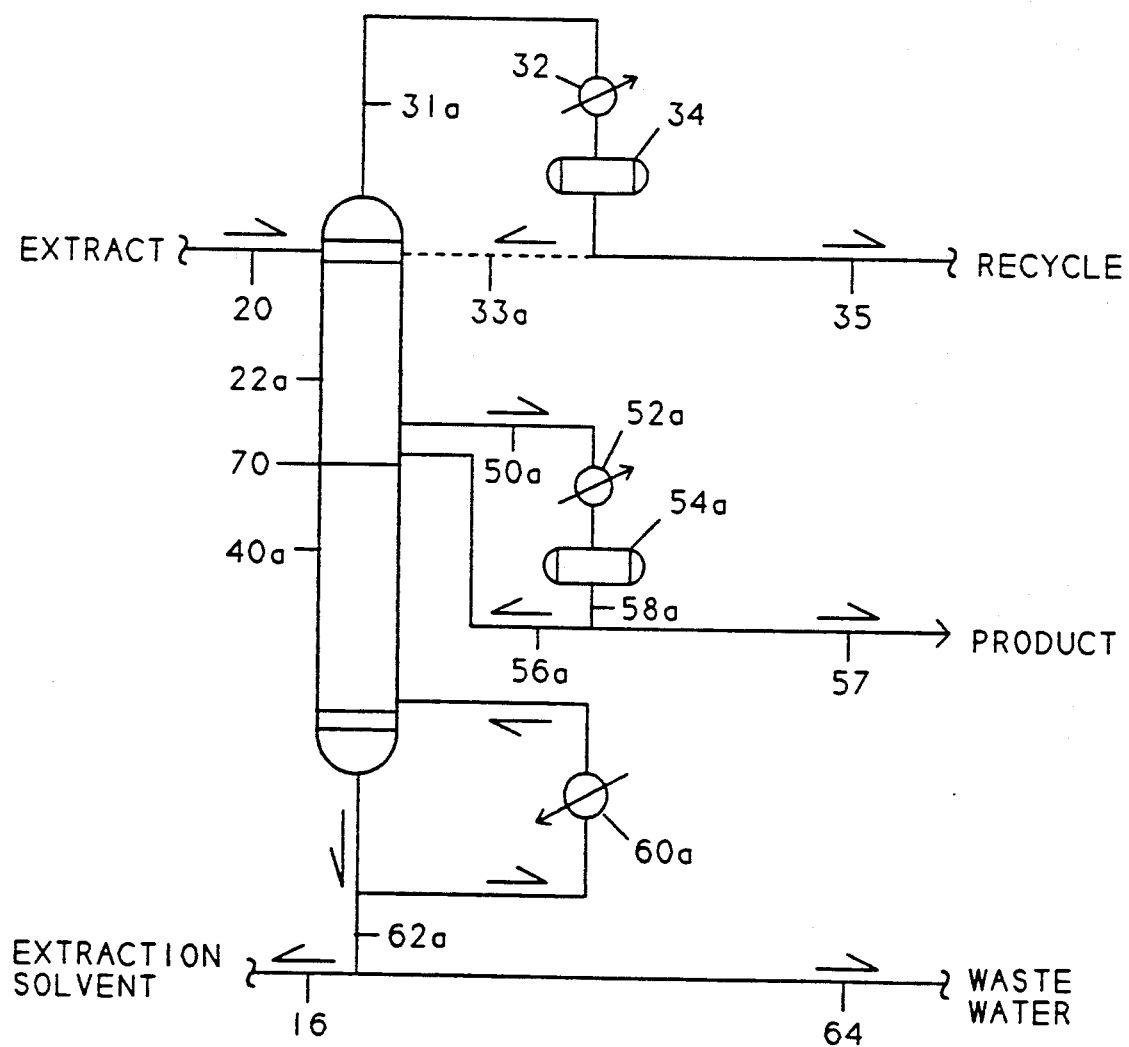
FIG. 3 is a schematic drawing illustrating a variation of the fractionation section of the apparatus shown in FIG. 2.

FIG. 3 illustrates a modification of the invention in which the stripping and fractionating operations are carried out in a single unit. In FIG. 3, the extract leaving extractor 2 enters the stripping section 22a of stripper-fractionator 70 through feed line 20. Similarly to the process carried out in the apparatus of FIG. 2, an overhead stream leaves the top of stripper-fractionator 70 through line 31a, is condensed in condenser 32, collected in accumulator 34 and recycled to extractor 2 through line 35. If desired, a portion of the condensate stream in accumulator 34 can be refluxed to column 70 through optional reflux line 33a, shown in dotted form. A side stream equivalent to the overhead stream in line 50 of FIG. 2 leaves stripper-fractionator 70 through line 50a, is condensed in condenser 52a and collected in accumulator 54a. Condensate leaving accumulator 54a through line 58a is split into two streams, a reflux stream which returns to stripper-fractionator 70 through line 56a and an ethanol-rich product stream which leaves the system through line 57. A bottoms stream leaves the fractionation section 40a of stripper-fractionator 70 through line 62a. A portion of the bottoms stream in line 62a is recycled to the bottom of stripper-fractionator 70 through reboiler 60a, and the remainder is split into an extractor solvent stream, which returns to extractor 2 via line 16, and a bottoms product waste water stream, which leaves the system through line 64. Stripper-fractionator 70 can be designed such that the composition of the streams leaving stripper-fractionator 70 through lines 35, 57 and 62a is substantially the same as the composition of the streams leaving the system of FIG. 2 through lines 35, 57 and 62 respectively.

Although the process of the invention is described above as a continuous process it can also be run as a batch process. In a batch operation the feed can be collected in tankage until a sufficient amount is available for a run. Similarly the various effluent streams from the process units can be collected and processed batch style. For example, the overhead stream from stripper 22 can be collected and held in tankage until it is desired to process it. It can then be fed to the extractor, either alone or mixed with fresh feed. In the same manner the waste water stream used as the extractor solvent can be stored in tankage until it is needed.

The invention is illustrated by the following examples, in which parts, percentages and ratios are on a weight basis, unless otherwise specified.

EXAMPLE 1

This example is based on a computer simulation run at continuous steady state conditions. The feed rates expressed in this example are in pounds per hour. Fresh feed (100 pounds per hour) comprised of 45 weight percent isopropyl acetate, 28 weight percent ethanol and 27 percent water is introduced into the system illustrated in FIG. 2. The fresh feed is combined with 9.2 pounds per hour of condensate coming from stripper 22. The condensate contains about 69.5 weight percent isopropyl acetate, 19.6 weight percent ethanol and 10.9 weight percent water. The combined feed stream is heated to a temperature of about 70 degrees C. in heat exchanger 14 and is introduced into extractor 2 through feed line 12.

Extractor 2 is operated during this run with a solvent stream comprising 150 pounds per hour of bottoms from fractionator 40 having a composition of 99.2 weight percent water and 0.8 weight percent ethanol. The solvent is cooled to a temperature of about 70 degrees C. in heat exchanger 14. The raffinate leaving extractor 2 amounts to 46.9 pounds per hour and contains 95.5 weight percent isopropyl acetate, 0.5 weight percent ethanol and 4.0 weight percent water. The extract stream leaving extractor 2 amounts to 212.3 pounds per hour.

The extract stream is introduced into stripper 22 at a temperature of about 70 degrees C. Stripper 22 is operated with 8 pounds per hour of recycled bottoms, which is heated to a temperature of about 88 degrees C. in heat exchanger 38. Condensate leaving accumulator 34 is at a temperature of about 75 degrees C. The bottoms product leaving stripper 22 (203.1 pounds per hour) contains 0.1 weight percent isopropyl acetate, 14.3 weight percent ethanol and 85.6 weight percent water and it is at a temperature of about 88 degrees C. An overhead product stream is obtained from fractionator 40 in an amount of 30.9 pounds per hour. This stream has a composition of 0.6 weight percent isopropyl acetate, 89.3 weight percent ethanol and 10.1 weight percent water. The bottoms product stream from fractionator 40, which amounts to 172.2 pounds per hour, has a composition of 99.2 weight percent water and 0.8 weight percent ethanol. The amount of this stream which is recycled to the extractor as solvent is 150 pounds per hour. The remaining portion, amounting to 22.2 pounds per hour, goes to waste treatment for disposal.

Example 1 illustrates the high theoretical separation efficiency and recovery obtained by the process of the invention.

Although the invention is illustrated with reference to a specific example, modifications of the example are contemplated. For example the extractor and/or the fractionators can be operated at conditions other than those used in the examples and the feed stream composition can be varied. Similarly, operations additional to those described can be employed. For instance, additional product purification steps may be used to remove undesired components from the product streams. Also, as noted above, equipment which is equivalent to the equipment described above can be used in the process of the invention. The scope of the invention is limited only by the breath of the appended claims.

What is claimed is:

1. A process for the recovery of isopropyl acetate and ethanol from a feed mixture comprising isopropyl acetate, ethanol and water comprising:
   a) introducing said feed mixture into a solvent extractor in which the solvent comprises water and recovering a high purity isopropyl acetate raffinate stream and an ethanol-rich extract stream,
   b) introducing said ethanol-rich extract stream to a first fractional distillation zone and producing an isopropyl acetate-rich stream and a substantially isopropyl acetate-free intermediate stream,
   c) recycling said isopropyl acetate-rich stream to said solvent extractor,
   d) introducing said substantially isopropyl acetate-free intermediate stream to a second fractional distillation zone and recovering a substantially azeotropic ethanol-water stream and a high purity water stream, and
   e) recycling said high purity water stream to said solvent extractor as solvent.

2. The process of claim 1 wherein said feed mixture comprises about 15 to about 90 weight percent isopropyl acetate and about 10 to about 70 weight percent ethanol.

3. The process of claim 1 carried out on a continuous basis.

4. The process of claim 1 wherein said isopropyl acetate-rich stream and said feed mixture are combined prior to introduction into said solvent extractor.

5. The process of claim 1 carried out on a batch basis.

6. The process of claim 5 wherein said feed mixture and said isopropyl acetate-rich stream are separately introduced into said solvent extractor.

7. The process of claim 1 wherein a portion of the isopropyl acetate-rich stream is returned to the top of the first fractional distillation zone as reflux.

8. The process of claim 1 wherein a portion of the substantially azeotropic ethanol-water stream is returned to the top of the second fractional distillation zone as reflux.

9. A process for the recovery of isopropyl acetate and ethanol from a feed mixture comprising isopropyl acetate, ethanol and water comprising:
   a) extracting said feed mixture in an extraction zone with water as the extraction solvent to recover a high purity isopropyl acetate raffinate stream and an ethanol-rich extract stream,
   b) stripping said ethanol-rich extract stream to produce an isopropyl acetate-rich stream and a substantially isopropyl acetate-free stream,
   c) recycling said isopropyl acetate-rich stream to said extraction zone,
   d) distilling said substantially isopropyl acetate-free stream to recover an ethanol-water stream and a high purity water stream, and
   e) recycling said high purity water stream as extraction solvent.

10. A process for the recovery of high purity isopropyl acetate from a feed mixture comprising isopropyl acetate, ethanol and water comprising:
    a) introducing said feed mixture into a solvent extractor in which the solvent comprises water and recovering a high purity isopropyl acetate raffinate stream and an ethanol-rich extract stream,
    b) introducing said ethanol-rich extract stream to a stripping zone and recovering an isopropyl acetate-rich stream and a substantially isopropyl acetate-free stream, and
    c) recycling said isopropyl acetate-rich stream to said solvent extractor.

11. A process for the recovery of high purity isopropyl acetate from a feed mixture comprising isopropyl acetate, ethanol and water comprising:
    a) extracting said feed mixture in an extraction zone with water as the extraction solvent to recover a high purity isopropyl acetate raffinate stream and an ethanol-rich extract stream,
    b) distilling said ethanol-rich extract stream to recover an isopropyl acetate-rich stream and a substantially isopropyl acetate-free stream, and
    c) recycling said isopropyl acetate-rich stream to said extraction zone.

12. A process for the recovery of isopropyl acetate and ethanol from a feed mixture comprising isopropyl acetate, ethanol and water comprising:
    a) contacting said feed mixture with water in an extraction zone to recover an isopropyl acetate-rich, substantially ethanol-free raffinate stream and an ethanol-rich extract stream,
    b) fractionally distilling said ethanol-rich extract stream to produce an isopropyl acetate-rich stream, an aqueous ethanol-rich, substantially isopropyl acetate-free stream and a high purity water stream, and
    c) recycling said isopropyl acetate-rich stream to said extraction zone.

13. The process of claim 12 wherein said fractionally distilling is carried out in a single unit.

14. The process of claim 12 wherein said fractionally distilling is carried out in two units.

* * * * *